(12) United States Patent
Dong et al.

(10) Patent No.: US 10,821,066 B2
(45) Date of Patent: Nov. 3, 2020

(54) ORAL CARE COMPOSITION FOR LONG-LASTING PEROXIDE DELIVERY

(71) Applicant: Colgate-Palmolive Company, New York, NY (US)

(72) Inventors: Rong Dong, Highland Park, NJ (US); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 19 days.

(21) Appl. No.: 15/867,784

(22) Filed: Jan. 11, 2018

(65) Prior Publication Data

US 2018/0193247 A1 Jul. 12, 2018

Related U.S. Application Data

(60) Provisional application No. 62/445,378, filed on Jan. 12, 2017.

(51) Int. Cl.
| | | |
|---|---|---|
| *A61K 8/81* | (2006.01) | |
| *A61Q 11/00* | (2006.01) | |
| *A61K 8/02* | (2006.01) | |
| *A61K 8/34* | (2006.01) | |
| *A61K 8/22* | (2006.01) | |

(52) U.S. Cl.
CPC .......... *A61K 8/8158* (2013.01); *A61K 8/0216* (2013.01); *A61K 8/22* (2013.01); *A61K 8/34* (2013.01); *A61K 8/8147* (2013.01); *A61K 8/8152* (2013.01); *A61K 8/8182* (2013.01); *A61Q 11/00* (2013.01)

(58) Field of Classification Search
CPC .................................. A61K 8/81; A61K 8/042
USPC .......................................................... 424/53
See application file for complete search history.

(56) References Cited

U.S. PATENT DOCUMENTS

| | | | |
|---|---|---|---|
| 8,883,212 B2 | 11/2014 | Pillai et al. | |
| 2005/0113510 A1 | 5/2005 | Singh | |
| 2005/0281757 A1* | 12/2005 | Ibrahim | A61Q 11/00 424/49 |
| 2006/0024246 A1 | 2/2006 | Ibrahim | |
| 2006/0263476 A1* | 11/2006 | Jani | A23G 4/20 426/3 |
| 2007/0122360 A1* | 5/2007 | Oniki | A61K 8/042 424/53 |
| 2007/0140991 A1* | 6/2007 | Maitra | A61K 8/8152 424/53 |
| 2007/0189983 A1* | 8/2007 | Gordon | A61K 8/73 424/53 |
| 2008/0305457 A1 | 12/2008 | Mitra | |
| 2014/0242001 A1 | 8/2014 | Pillai et al. | |
| 2015/0257983 A1* | 9/2015 | Lendenmann | A61K 6/0017 424/78.02 |
| 2016/0296427 A1* | 10/2016 | Young | A61K 8/65 |

FOREIGN PATENT DOCUMENTS

| | | |
|---|---|---|
| DE | 12010062611 A1 | 6/2012 |
| RU | 2359707 | 6/2009 |
| RU | 2416433 | 4/2011 |
| RU | 2517142 | 5/2014 |
| RU | 2662305 | 7/2018 |
| WO | WO 2016/131642 | 8/2016 |

OTHER PUBLICATIONS

International Search Report and Written Opinion of the International Searching Authority in International Application No. PCT/US2018/013242, dated Apr. 26, 2018.

* cited by examiner

*Primary Examiner* — Walter E Webb

(57) ABSTRACT

A tooth whitening composition includes a hydrophobic copolymer, a hydrophilic whitening agent and a polar solvent.

16 Claims, No Drawings

ORAL CARE COMPOSITION FOR LONG-LASTING PEROXIDE DELIVERY

BACKGROUND

Many substances can stain or reduce the whiteness of one's teeth. In particular, the foods, tobacco products, and fluids that one consumes tend to stain one's teeth. These products or substances tend to accumulate on the enamel layer of the tooth and form a pellicle film over the teeth. Tooth whitening compositions, containing an active tooth whitening agent, may be used to reduce staining and whiten teeth. Certain whitening agents, like peroxide, can present formulation difficulties, due to the volatility and reactivity of the peroxide.

It would be advantageous to provide sustained delivery of the active tooth whitening agent. However, polymer delivery systems for application of tooth whitening compositions to the teeth have in general not proved sufficiently durable to remain on the teeth for extended periods. Among other reasons, the teeth are physically abraded by brushing and chewing and are moreover exposed to a wide range of temperatures and pH levels as a result of eating and drinking. Under ordinary conditions, therefore, most polymers will not remain on the teeth for very long. Additionally, such systems may result in discomfort or unpleasant mouth-feel to the user. Moreover, it is desirable that the materials of the tooth whitening compositions themselves, including the polymers in the polymer delivery system, do not readily take up stain or otherwise discolor the teeth.

BRIEF SUMMARY

The present disclosures provide a tooth whitening composition, including: a hydrophobic copolymer; a hydrophilic whitening agent; and a polar solvent.

In an implementation of the disclosed tooth whitening composition, the hydrophobic copolymer is a film-forming hydrophobic copolymer.

In an implementation of the disclosed tooth whitening composition, the film-forming hydrophobic copolymer comprises functional groups configured to adhere to a tooth surface.

In an implementation of the disclosed tooth whitening composition, the hydrophobic copolymer comprises an acrylate.

In an implementation of any of the disclosed tooth whitening compositions, the hydrophobic copolymer comprises at least one of acrylate/octylacrylamide copolymer, VA/Butyl Maleate/Isobornyl Acrylate copolymer, Acrylates/t-Butylacrylamide copolymer, polyvinylpyrrolidone/vinyl acetate copolymer, triacontanyl PVP copolymer, Acrylates/Dimethylaminoethyl Methacrylate copolymer, or mixtures thereof.

In an implementation of any of the disclosed tooth whitening compositions, the hydrophobic copolymer comprises 2-propenoic acid, 2-methyl-, 2-methylpropyl ester, polymer with 2-propenoic acid and N-(1,1,3,3-tetramethylbutyl)-2-propenamide.

In an implementation of any of the disclosed tooth whitening compositions, the hydrophobic copolymer is present in an amount of from greater than about 0% to about 300, by weight.

In an implementation of any of the disclosed tooth whitening compositions, the hydrophilic whitening agent comprises a peroxide.

In an implementation of any of the disclosed tooth whitening compositions, the whitening agent comprises hydrogen peroxide.

In an implementation of any of the disclosed tooth whitening compositions, the hydrophobic copolymer is present in an amount of from greater than about 0% to about 12%, by weight.

In an implementation of any of the disclosed tooth whitening compositions, the polar solvent comprises ethanol.

In an implementation of any of the disclosed tooth whitening compositions, the composition is an orally acceptable composition.

In an implementation of any of the disclosed tooth whitening compositions, the composition is a film-forming composition.

In an implementation of any of the disclosed tooth whitening compositions, the composition is in the form of a liquid.

In an implementation of any of the disclosed tooth whitening compositions, the composition is in the form of a gel.

In an implementation of any of the disclosed tooth whitening compositions, the composition does not comprise a non-polar solvent.

In an implementation of any of the disclosed tooth whitening compositions, the composition does not comprise a suspension.

Also provided herein is a method of forming any of the disclosed tooth whitening compositions, comprising: combining the hydrophobic copolymer, the hydrophilic whitening agent, and the polar solvent.

Also provided herein is a method for whitening a surface of a tooth comprising: contacting the surface of the tooth with any of the disclosed tooth whitening compositions for a duration of time sufficient to effect whitening of the surface of the tooth.

In an implementation of the method for whitening a surface of a tooth, wherein the contacting of the surface of the tooth with any of the disclosed tooth whitening composition comprises forming a hydrophobic film comprising the hydrophobic polymer and the whitening agent, and wherein the duration of time sufficient to effect whitening of the surface of the tooth comprises diffusing the whitening agent from the hydrophobic film to the tooth surface over a period of time comprising from about 5 minutes to about 12 hours.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The term "hydrophobic" as applied to polymers and copolymers and employed herein refers to an organic polymer or copolymer which is substantially non-aqueous and having a water solubility of less than 0.1% g/g water at a pH of 8 pH and below.

The term "hydrophilic" is used herein consistent with its standard meaning of having affinity for water.

As used herein, "film-forming composition" refers to a material or combination of materials that may precipitate out of solution, for example, as the composition dries upon application to a surface (e.g., as solvent evaporates away), thereby leaving behind a film of the precipitated material or combination of materials.

As used herein, "orally acceptable" refers to a material or combination of materials that are safe for use in the compositions of the present disclosure, commensurate with a reasonable benefit/risk ratio, with which the whitening agent, and other desired active ingredients may be associated while retaining significant efficacy.

Tooth Whitening Composition

Described herein are improved, tooth whitening compositions having excellent film-forming and whitening agent delivery properties.

In an implementation, a tooth whitening composition comprises: a hydrophobic copolymer; a hydrophilic whitening agent; and a polar solvent. In one aspect, the tooth whitening composition includes, on a weight basis, 0.1% to 60%, more preferably 1% to 30%, even more preferably 2% to 25% of the hydrophobic copolymer. In one aspect, the tooth whitening composition includes, on a weight basis 0.01% to 40%, more preferably 0.05% to 25%, even more preferably 0.08% to 20% of the hydrophilic whitening agent. In one aspect, the tooth whitening composition includes, on a weight basis, 10% to 95%, more preferably 20% to 80%, even more preferably 30% to 70% of the polar solvent.

The improved tooth whitening compositions exhibit good mouth feel and tooth whitening property. For example, in an implementation, the tooth whitening composition preferably does not comprise a suspension and is free of solid particulate. This is because the hydrophobic copolymer may be dissolved in the polar solvent. Accordingly, the composition preferably does not comprise a non-polar solvent. The film-forming composition may be delivered to a tooth surface with or without use of an applicator, and preferably is delivered directly by rinsing in the user's mouth. Regardless of the method of delivery, the polar solvent may be volatile such that when the tooth whitening composition contacts a tooth surface, enough of the polar solvent may evaporate, leaving behind a film of the hydrophobic copolymer (e.g., a film-forming hydrophobic copolymer) with the hydrophilic whitening agent embedded therein, but able to diffuse out and reach the tooth's enamel. Additionally, as a result of the relative amounts of hydrophobic copolymer and hydrophilic whitening agent used in the formulation, the tooth whitening composition provides a good balance of hydrophobicity and hydrophilicity. That is, the composition, upon drying, is hydrophilic enough to release peroxide molecules (e.g., via diffusion out of the film) to a tooth surface in an amount effective for providing good whitening efficacy (e.g., dW change of 2 after one treatment), and is also hydrophobic enough to remain in place on a tooth surface for a prolonged period (e.g., up to 5 minutes or longer, for example up to 10 minutes or longer) to provide long-lasting peroxide delivery benefit.

Hydrophobic Film-Forming Copolymer

In various implementations, the tooth whitening compositions disclosed herein comprise a hydrophobic film-forming copolymer having functional groups with properties that provide for good adhesion to a tooth surface. Examples of such functional groups, include but are not limited to: carboxylic acid, phosphate, hydroxyl, amine, disulfide, nitro, etc. The hydrophobic copolymer may be selected from a carboxylated acrylic copolymer such as a copolymer of octylacrylamide and one or more monomers comprising acrylic acid, methacrylic acid, or one or more simple esters thereof. The hydrophobic copolymer of the tooth whitening compositions may be an acrylate/octylacrylamide copolymer. In one implementation, the hydrophobic copolymer preferably comprises a copolymer (e.g., 2, 3 or 4 monomers), for example, 2-Propenoic acid, 2-methyl-, 2-methylpropyl ester; polymer with 2-propenoic acid; and N-(1,1,3,3-tetramethylbutyl)-2-propenamide (CAS 129702-02-9) which is available as DEMACRYL® 79 from AkzoNobel Surface Chemistry LLC (Chicago, Ill.). Other examples include but are not limited to AMPHOMER® 4961, AMPHOMER® HC, DERMACRYL® 2.0, RESYN™ XP, all from AkzoNobel Surface Chemistry LLC (Chicago, Ill.). The hydrophobic copolymer may also be selected from Octylacrylamide/Acrylates/Butylaminoethyl Methacrylate Copolymer, such as AMPHOMER LV-71, AMPHOMER, AMPHOMER® EDGE™, BALANCE 47, all from AkzoNobel Surface Chemistry LLC (Chicago, Ill.). The hydrophobic copolymer may also be selected from VA/Butyl Maleate/Isobornyl Acrylate Copolymer, such as Advantage™ Plus from Ashland Global Specialty Chemicals Inc. (Covington, Ky.). The hydrophobic copolymer may also be selected from Acrylates/t-Butylacrylamide Copolymer, such as Ultrahold® Strong and Ultrahold®8 from BASF SE (Ludwigshafen, Germany). The hydrophobic copolymer may also be selected from Acrylates/Dimethylaminoethyl Methacrylate Copolymer, such as Eudragit® range of polymers from Evonik Industries (Essen, Germany), such as Eudragit® E100, Eudragit® E PO, Eudragit® RS 100, Eudragit® RS PO, Eudragit® RL PO, Eudragit® RL 100 etc. The hydrophobic copolymer may also be selected from polyvinylpyrrolidone/vinyl acetate, such as PVP/VA series of polymers from Ashland Global Specialty Chemicals Inc. (Covington, Ky.). The hydrophobic copolymer may also be selected from triacontanyl PVP, such as Ganex™ WP-660 from Ashland Global Specialty Chemicals Inc. (Covington, Ky.). The hydrophobic copolymer may be selected from at least one of Octylacrylamide/Acrylates/Butylaminoethyl Methacrylate copolymer, VA/Butyl Maleate/Isobornyl Acrylate copolymer, Acrylates/t-Butylacrylamide copolymer, polyvinylpyrrolidone/vinyl acetate copolymer, triacontanyl PVP copolymer, Acrylates/Dimethylaminoethyl Methacrylate copolymer, or mixtures thereof In various implementations, the hydrophobic copolymer is present in the tooth whitening composition in an amount of up to about 60%, including from greater than about 0% to about 30%, more preferably from about 5% to about 25%, or from about 10% to about 20%, most preferably including an amount of about 15% by weight relative to the total weight of the tooth whitening composition.

Hydrophilic Whitening Agent

In various implementations, the tooth whitening compositions disclosed herein comprise at least one whitening agent as an active ingredient. In certain implementations, the at least one whitening agent is a peroxide compound. As further discussed below, a "whitening agent" is a material which affects whitening of a tooth surface to which it is applied.

As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxy phthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various implementations, the peroxide compound comprises hydrogen peroxide, urea peroxide, sodium percarbonate and mixtures thereof.

Peroxide releasing compounds that may be mentioned for use in the tooth whitening compositions disclosed herein include peroxide containing compounds such as urea peroxide, sodium percarbonate, sodium perborate and polyvinylpyrrolidone-$H_2O_2$ complexes (hereinafter "PVP-$H_2O_2$"). Polyvinylpyrrolidone is also known as poly-N-vinyl-poly-2-pyrrolidone and commonly abbreviated to "PVP". PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar amide group, four non-polar methylene groups and a non-polar methane group.

Both linear and cross-linked complexes of PVP-$H_2O_2$ are known in the art, and PVP-$H_2O_2$ is considered to be stable in an anhydrous environment. Upon exposure to highly aqueous environments, such as in the oral cavity, the PVP-$H_2O_2$ dissociates into individual species (PVP polymer and $H_2O_2$). In one preferred implementation, the PVP-$H_2O_2$ complex is 80% by weight polyvinylpyrrolidone and 20% by weight $H_2O_2$.

In alternate embodiments disclosed herein, the at least one whitening agent comprises a liquid hydrogen peroxide solution. Typically, the liquid hydrogen peroxide comprises $H_2O_2$ contained in an aqueous water-based solution (e.g., 35 wt % aqueous $H_2O_2$ solution).

In various embodiments, the at least one whitening agent is present in the tooth whitening composition in an amount of up to about 40%, including from about 0% to 40%, including from greater than about 0% to about 30%, more preferably from about 0.1% to about 20%, or from about 0.3% to about 12%, including an amount of about 6% by weight relative to the total weight of the tooth whitening composition.

Additionally, at least one stabilizer may be present with a composition that includes the whitening agent. Stabilizers can be selected from, for example, kelating agents, polyphosphates, peroxide stabilizers, and free radicals. In an implementation, acetanilide or a similar organic material may be used with a pyrophosphate stabilizer such as sodium acid pyrophosphate. In an implementation, a hydrogen peroxide solution with at least one stabilizer may be used as the whitening agent.

Polar Solvent

In various implementations, the tooth cleaning composition disclosed herein includes a polar solvent. The polar solvent is selected such that it is capable of at least partially dissolving the hydrophobic copolymer. The polar solvent may comprise glycerin, propylene glycol, alcohol, or water.

Preferably, the polar solvent comprises ethanol, for example, in an amount sufficient to dissolve the ingredients of the tooth whitening composition, in particular the hydrophobic polymer. In various implementations, the polar solvent is present in the tooth whitening composition in an amount of up to about 99%, including from greater than about 0% to about 99%, more preferably from about 10% to about 95%, or from about 20% to about 80%, most preferably including an amount of about 79% by weight relative to the total weight of the tooth whitening composition.

Preferably the polar solvent is selected so that it does not react with, or only minimally reacts with, the whitening agent. For example, some polar solvents are known to decompose hydrogen peroxide and would, therefore, reduce the shelf-life of tooth whitening compositions envisioned herein. However, decomposition of the hydrogen peroxide does not necessarily result from reaction with some polar solvents. For example, peroxides may undergo self-decomposition. Nonetheless, incompatible solvents in a tooth whitening composition may accelerate the self-decomposition of hydrogen peroxide. Accordingly, acceptable ingredients, including the polar solvent(s), are those that form a tooth whitening composition capable of retaining 60% or greater of the peroxide active, for example, on aging for 13 weeks at 40° C.

Additional Ingredients

Other ingredients may further be included in the whitening compositions of the present invention, and include surfactants, thickening agents, flavoring agents, sweetening agents, desensitizing agents, anti-microbial agents, anti-caries agents, anti-calculus agents, anti-inflammatory agents, vitamins, pigments and coloring agents, enzymes, preservatives, abrasive agents, and tartar control agents, for example.

Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine.

In some implementations, the composition optionally comprises a thickening agent. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as CARBOWAX, available from The Dow Chemical Company), cellulosic polymers such as hydroxyethylcellulose, ethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same.

In certain embodiments disclosed herein, the tooth whitening composition may further comprise at least one flavoring agent. The at least one flavoring agent, may, for example, be selected from essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen.

In embodiments where the tooth whitening composition is sweetened, at least one sweetening agent may be used as an alternative or as a complement to the at least one flavoring agent. Suitable sweetening agents may be water-soluble and include, for example, sodium saccharin, sodium cyclamate, xylitol, perillartien, D-tryptophan, aspartame, dihydrochalcones and the like.

Exemplary antimicrobial agents may include those typically used in oral care compositions, such as Thymol, benzyl alcohol, Triclosan, chlorhexidine, stannous salts including copper-, zinc- and stannous salts such as zinc oxide, zinc lactate, zinc citrate, zinc sulfate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine, and halogenated bisphenolic compounds, such as 2,2'methylen-ebis-(4-chloro-6-bromophenol).

Some embodiments of the present disclosure comprises pigment(s) and/or coloring agent(s). Any orally acceptable pigment and/or colorant can be used, but typically, type, fineness (particle size) and amount of pigment and/or colorant should be selected so that tooth enamel is not excessively abraded in normal use of the tooth whitening composition. Average particle size of an pigment and/or colorant, if present, is generally about 0.1 to about 30 μm for example about 1 to about 20 μm or about 5 to about 15 μm. In an implementation, pigment or colorant comprise $TiO_2$ and/or $ZnO$. Inclusion of pigment and/or colorant can provide for instant whitening effect due to, for example, the opacity of the pigment particles from the composition being deposited on a tooth surface while the whitening agent is transported from the composition and into the tooth enamel to remove stains.

In various implementations, any one of the tooth whitening compositions described herein comprises an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of about 0.1% to about 30% w/w. In some embodiments, the stable whitening dentifrice composition comprises a mixture of anticalculus agents. In some embodiments, tetrapotassium pyrophosphate (TKPP), tetrasodium pyrophosphate (TSPP) and sodium tripolyphosphate (STPP) are used as the anticalculus agents.

Another desirable additional ingredient of the present tooth whitening compositions is a synthetic anionic polymeric polycarboxylate (SAPP), which acts as a stabilizer for the polyphosphate anti-tartar agent and may help to block access of painful or pain-causing materials, such as sugars, to the tooth nerves.

Exemplary anti-inflammatory agents may include those typically used in oral care compositions, such as ibuprofen, flurbiprofen, aspirin, and indomethacine. Exemplary anti-caries agents may include ingredients such as sodium-, calcium-, magnesium- and stannous fluoride, aminefluorides, disodium monofluorophosphate and sodium trimetaphosphate. Exemplary vitamins may include ingredients such as Vitamin C. Exemplary desensitizing agents may include ingredients such as potassium citrate, potassium chloride, potassium tartrate, potassium bicarbonate, potassium oxalate, potassium nitrate and strontium salts. Exemplary anti-calculus agents may include ingredients such as pyrophosphate salts including the mono, di, tri and tetra alkali metal and ammonium pyrophosphate and tripolyphosphate salts. Exemplary enzymes may include glucoamylase.

Some implementations provide tooth whitening compositions wherein at least one of ingredients is a fluoride ion source selected from stannous fluoride, sodium fluoride, potassium fluoride, sodium monofluorophosphate, sodium fluorosilicate, ammonium fluorosilicate, amine fluoride, and ammonium fluoride.

Also disclosed herein are methods for whitening a surface of a tooth in an oral cavity of a human or other animal subject. One such method comprises (a) applying a tooth whitening composition as disclosed herein to the tooth surface to be whitened for a plurality of minutes per day; and (b) repeating step (a) for multiple days to thereby whiten the teeth.

Exemplary methods disclosed herein comprise contacting the tooth whitening composition with the surface of the tooth. In an implementation, the contacting of the surface of the tooth with the tooth whitening composition comprises forming a hydrophobic film comprising the hydrophobic polymer and the whitening agent on the surface of the tooth. The contacting may occur for a duration of time sufficient to satisfactorily affect whitening of the teeth. In an implementation, the duration of time sufficient to effect whitening of the surface of the tooth comprises diffusing the whitening agent from the hydrophobic film to the tooth surface over a period of time comprising from 2 minutes to about 24 hours. Thus, the contacting may occur for a sufficient period of time to at least partially whiten teeth. This can be a period of time ranging from about 2 minute to about 24 hours or longer. In certain implementations, the tooth whitening composition dries (e.g., via evaporation of the polar solvent) and forms a film that may remain on the tooth surface for a period of time ranging from about 2 minute to about 24 hours, from about 5 minute to about 12 hours, from about 10 minutes to about 8 hours, or from about 15 minutes to about 6 hours, or from about 30 minutes to about 4 hours or for a period of time sufficient to satisfactorily affect whitening of the teeth.

In certain implementations disclosed herein, a tooth whitening composition, which may be substantially non-aqueous or may be aqueous, may be effective over a longer period of time, since it is not significantly diluted or washed away in the oral cavity during the treatment time. The tooth whitening composition can be removed as and when required, at will, by an employment of standard oral hygiene procedures such as brushing or by rinsing with an alcoholic mouthwash. While in place, the composition may release agents contained therein at a slow, relatively constant rate and in concentration sufficient to effect stain removal from or whitening of the teeth.

Further disclosed herein are methods of making the present tooth whitening compositions. In an example, any one of the tooth whitening compositions disclosed herein may be prepared by adding and mixing the ingredients of the composition in a suitable vessel, such as a stainless steel tank provided with a mixer. In the preparation of the tooth whitening composition, the ingredients may be added to the mixer in the following or in any order: the hydrophobic copolymer, the hydrophilic whitening agent; the polar solvent, and one or more of the additional ingredients. The ingredients may then be mixed to form a homogenous composition.

In an implementation, the tooth whitening compositions disclosed herein may be used in the manufacture of an oral care product for protecting the teeth from staining, bacteria, or for whitening teeth.

In an implementation, the tooth whitening compositions disclosed herein may be prepared in the form of a flowable composition, such as a liquid, or as a viscous liquid dispersion, such as a gel. In an implementation, the tooth whitening compositions disclosed herein may be used in a method of protecting the teeth from staining or bacteria, for example, by applying any of the foregoing compositions to the teeth.

The tooth whitening composition may be introduced to the mouth directly, such as by rinsing (e.g., the user swirls the composition in the mouth like mouthwash). That is, preferably, application of any of the tooth whitening compositions leaves behind a film comprising the hydrophobic copolymer and the hydrophilic whitening agent on the teeth.

Alternatively, the tooth whitening compositions may be applied directly onto the user's teeth with an applicator, such as by painting the teeth with an applicator brush or an applicator pen. Accordingly, in at least one implementation, a package comprises any of the foregoing tooth whitening compositions together with an applicator for applying the composition to the teeth.

Alternatively, the tooth whitening compositions may be applied directly onto the user's teeth via placement of the composition on a substrate, such as a strip or mouth-tray. For example, any one of the tooth whitening compositions described above can be poured or spread onto a surface of the substrate and then the substrate may be placed in the user's mouth to place the composition in contact with the tooth surface. The substrate may remain in place or may be removed, leaving at least some of the composition on the surface of at least one tooth in the user's mouth.

EXAMPLES

Example 1

An exemplary tooth whitening composition according to the formulations described herein was prepared. The tooth whitening composition included 10-20% of DEMACRYL® 79 as the hydrophobic copolymer, and 0.3-12% hydrogen peroxide (35%) solution as the hydrophilic whitening agent (available from Arkema, Inc. of King of Prussia, Pa.), and the remainder with 200 proof anhydrous ethanol (EtOH) as the polar solvent (available from Pharmco-Products, Inc. d/b/a Pharmco-Aaper of Shelbyville, Ky.).

The composition was prepared by adding the DEMACRYL® 79 and EtOH to form a mixture in a spin mix jar. The mixture was then spin-mixed at 3540 rpm for four minutes. The hydrogen peroxide solution was added to the mixture in the jar comprising the DEMACRYL® 79 and the EtOH and mixed at 3540 rpm until a homogenous, clear solution was obtained. The resulting formulation of the tooth whitening composition, including a listing of the ingredients listed by wt % and total weight is provided in Table 1.

| Formula 1 | % | Weight (g) |
|---|---|---|
| DEMACRYL ® 79 | 15.0% | 1.5 |
| Hydrogen Peroxide (35%) | 6.0% | 0.6 |
| EtOH | 79.0% | 7.9 |
| total | 100.00% | 10 |

Example 2

Another exemplary tooth whitening composition according to the formulations described herein was prepared. The tooth whitening composition included 10-20% of Eudragit® E100 as the hydrophobic copolymer, and 0.3-12% hydrogen peroxide (35%) solution as the hydrophilic whitening agent (available from Arkema, Inc. of King of Prussia, Pa.), and the remainder with 200 proof anhydrous ethanol (EtOH) as the polar solvent (available from Pharmco-Products, Inc. d/b/a Pharmco-Aaper of Shelbyville, Ky.).

The composition was prepared by adding the Eudragit® E100 and EtOH to form a mixture in a spin mix jar. The mixture was then spin-mixed at 3540 rpm for four minutes. The hydrogen peroxide solution was added to the mixture in the jar comprising the Eudragit® E100 and the EtOH and mixed at 3540 rpm until a homogenous, clear solution was obtained. The resulting formulation of the tooth whitening composition, including a listing of the ingredients listed by wt % and total weight is provided in Table 2.

| Formula 2 | % | Weight (g) |
|---|---|---|
| Eudragit ®E100 | 15.0% | 1.5 |
| Hydrogen Peroxide (35%) | 6.0% | 0.6 |
| EtOH | 79.0% | 7.9 |
| total | 100.00% | 10 |

Example 3—Tooth Whitening

The whitening performance of the tooth whitening composition of Example 1 was assessed using artificially stained bovine tooth blocks (incisors mounted in an acrylic resin) purchased from Dental Product Testing Therametric Technologies, Inc. Three of the stained bovine tooth blocks with L values of 60-65 were cleaned and wiped dry. The L, a, b values were measured by a MHT SpectroShade. The tooth blocks were coated with the tooth whitening composition according to Example 1 using a nail polish brush. The composition was air dried for 3-5 minutes to allow the EtOH to evaporate, leaving behind a film comprising the hydrogen peroxide and the DERMACRYL® 79 coated on the tooth blocks.

The coated blocks were immersed in artificial saliva in 12 well plates and incubated at 37° C. with 100 rpm agitation overnight. This allowed at least some of the hydrogen peroxide to diffuse out from the film and interact with the tooth blocks. The next morning, the tooth blocks were taken out from the artificial saliva and the remaining film was removed by wiping with ethanol. L, a, b values were measured again using SpectroShade. This procedure was repeated so that the tooth blocks received five treatments with the film-forming cleaning composition.

Whitening performance was reported as a change of W value ($\Delta W$) after each treatment compared to baseline value according to:

$$W^* = ((a^*)^2 + (b^*)^2 + (L^* - 100)^2)^{1/2} \text{ and}$$

$$\Delta W^* = W^*_{treated} - W^*_{baseline}.$$

|  | First Treatment | Second Treatment | Third Treatment | Fourth Treatment | Fifth Treatment |
|---|---|---|---|---|---|
| Avg. $\Delta W$ | −3.79 | −7.41 | −8.18 | −10.48 | −15.25 |
| Std. | 2.19 | 1.53 | 2.51 | 2.29 | 1.71 |

Example 4—Aging Study

Accelerated aging of the tooth whitening composition of Example 1 was performed. For 13 weeks, the composition of Example 1 (stored in 4 individual tubes) was kept at 40° C. in a test chamber having 75% humidity and the active oxygen (AO %). After 13 weeks, 85.2% active oxygen remained in the composition, indicating that the peroxide molecules of the composition are stable.

As shown in Table 2 above, $\Delta W$ was calculated to be −15.25 after the 5th treatment. Comparatively, conventional whitening gel having a higher concentration of peroxide than the composition of Example 1 can reach $\Delta W$ of ~−12 after one to two weeks of treatment. While not limited to any particular theory it is believed that the superior whitening efficacy of the tooth whitening compositions described herein comprising a hydrophobic copolymer, whitening agent, and polar solvent, including the composition as reported for Example 1 above, is attributed to its long lasting property (i.e., long residence time); that is, its ability to form a film or coating on surfaces for delivery of the whitening agent and its ability to controllably release the whitening agent as evidenced by the results of the aging study. In short, this prolonged durability of the tooth whitening composition described herein allows coatings and films formed therefrom to deliver whitening agent, such as hydrogen peroxide, over a long period of time, and at a location close to teeth surface to remove stain molecules from teeth.

ADDITIONAL EMBODIMENTS

In an aspect, there is a method of forming the tooth whitening composition, comprising: combining a hydrophobic copolymer, a hydrophilic whitening agent, and a polar solvent. In an implementation of this method, the hydrophobic copolymer comprises an acrylate. In an implementation of this method, the hydrophobic copolymer is an acrylate/octylacrylamide copolymer. In an implementation of this method, the hydrophobic copolymer comprises 2-propenoic acid, 2-methyl-, 2-methylpropyl ester, polymer with 2-propenoic acid and N-(1,1,3,3-tetramethylbutyl)-2-propenamide. In an implementation of this method, the hydrophobic copolymer is present in an amount of from greater than about 0% to about 30%, by weight. In an implementation of this method, the hydrophilic whitening agent comprises a peroxide. In an implementation of this method, the whitening agent comprises hydrogen peroxide. In an implementation of this method, the hydrophobic copolymer is present in an amount of from greater than about 0% to about 12%, by weight. In an implementation of this method, the polar solvent comprises ethanol.

What is claimed is:

1. A tooth whitening composition in the form of a liquid flowable composition, or in the form of a viscous liquid dispersion or a gel, consisting of:
  a hydrophobic copolymer, wherein the hydrophobic copolymer is a film forming hydrophobic polymer consisting essentially of 2-propenoic acid, 2-methyl-, 2-methylpropyl ester, polymer with 2-propenoic acid and N-(1,1,3,3-tetramethylbutyl)-2-propenamide, Acrylates/Dimethylaminoethyl Methacrylate copolymer, or mixtures thereof;
  a hydrophilic whitening agent, wherein the hydrophilic whitening agent consists essentially of hydrogen peroxide 35%; and
  a polar solvent, wherein the polar solvent consists essentially of ethanol.

2. The tooth whitening composition of claim 1, wherein the hydrophobic copolymer consists essentially of 2-propenoic acid, 2-methyl-, 2-methylpropyl ester, polymer with 2-propenoic acid and N-(1,1,3,3-tetramethylbutyl)-2-propenamide.

3. The tooth whitening composition of claim 1, wherein the hydrophobic copolymer is present in an amount of from greater than about 10% to about 20%, by weight.

4. The tooth whitening composition of claim 1, wherein the hydrogen peroxide 35% is present in an amount from 0.3% to about 12% by weight.

5. The tooth whitening composition of claim 1, wherein the hydrophobic copolymer is present in an amount of about 15%, by weight.

6. The tooth whitening composition of claim 1, wherein the composition is an orally acceptable composition.

7. The tooth whitening composition of claim 1, wherein the composition is a film-forming composition.

8. The tooth whitening composition of claim 1, wherein the composition is in the form of a liquid.

9. The tooth whitening composition of claim 1, wherein the composition is in the form of a gel.

10. The tooth whitening composition of claim 1, wherein the composition does not comprise a non-polar solvent.

11. The tooth whitening composition of claim 1, wherein the composition does not comprise a suspension.

12. The tooth whitening composition of claim 1, wherein the hydrophobic copolymer comprises a hydrophobic film-forming copolymer comprising functional groups configured to adhere to a tooth surface.

13. A method of forming the tooth whitening composition of claim 1, consisting of: combining the hydrophobic copolymer, the hydrophilic whitening agent, and the polar solvent.

14. A method for whitening a surface of a tooth comprising: contacting the surface of the tooth with the tooth whitening composition of claim 1 for a duration of time sufficient to effect whitening of the surface of the tooth.

15. The method of claim 14, wherein the contacting of the surface of the tooth with the tooth whitening composition comprises forming a hydrophobic film comprising the hydrophobic polymer and the whitening agent, and wherein the duration of time sufficient to effect whitening of the surface of the tooth comprises diffusing the whitening agent from the hydrophobic film to the tooth surface over a period of time comprising from about 5 minutes to about 12 hours.

16. The tooth whitening composition of claim 1, wherein the hydrogen peroxide 35% is present in an amount of about 6% by weight.

\* \* \* \* \*

UNITED STATES PATENT AND TRADEMARK OFFICE
CERTIFICATE OF CORRECTION

PATENT NO. : 10,821,066 B2
APPLICATION NO. : 15/867784
DATED : November 3, 2020
INVENTOR(S) : Rong Dong et al.

Page 1 of 1

It is certified that error appears in the above-identified patent and that said Letters Patent is hereby corrected as shown below:

In the Specification

In Column 1, Line 63, delete "300," and insert -- 30%, --, therefor.

Signed and Sealed this
Fifth Day of January, 2021

Andrei Iancu
*Director of the United States Patent and Trademark Office*